(12) United States Patent
Feng et al.

(10) Patent No.: US 8,900,855 B2
(45) Date of Patent: Dec. 2, 2014

(54) PH SENSOR INTEGRATION TO SINGLE USE BIOREACTOR/MIXER

(75) Inventors: Chang-Dong Feng, Long Beach, CA (US); Barry W. Benton, Orange, CA (US); Dave Anderson, Costa Mesa, CA (US); Fong S. Yang, Tustin, CA (US); Wayne B. Wood, Silverado, CA (US)

(73) Assignee: Rosemount Analytical Inc., Irvine, CA (US)

( * ) Notice: Subject to any disclaimer, the term of this patent is extended or adjusted under 35 U.S.C. 154(b) by 0 days.

(21) Appl. No.: 13/325,254

(22) Filed: Dec. 14, 2011

(65) Prior Publication Data

US 2012/0178153 A1  Jul. 12, 2012

Related U.S. Application Data (60) Provisional application No. 61/424,246, filed on Dec. 17, 2010.

(51) Int. Cl.
| | | |
|---|---|---|
| *C12M 1/00* | (2006.01) | |
| *C12M 3/00* | (2006.01) | |
| *C12M 1/12* | (2006.01) | |
| *C12M 1/26* | (2006.01) | |
| *C12C 1/15* | (2006.01) | |
| *C12C 7/06* | (2006.01) | |
| *C12M 1/34* | (2006.01) | |

(52) U.S. Cl.
CPC ................ *C12M 23/14* (2013.01); *C12M 41/26* (2013.01); *C12M 41/32* (2013.01); *C12M 41/34* (2013.01)
USPC .................. 435/289.1; 435/283.1; 435/291.8; 435/297.1; 435/309.2

(58) Field of Classification Search
CPC ...... C12M 23/14; C12M 41/26; C12M 41/32; C12M 41/34
USPC ............................................ 435/283.1–309.4
See application file for complete search history.

(56) References Cited

U.S. PATENT DOCUMENTS

| | | | |
|---|---|---|---|
| 6,602,401 B1 | 8/2003 | Feng ............................ | 205/783 |
| 6,894,502 B2 | 5/2005 | Feng et al. .................... | 324/438 |

(Continued)

FOREIGN PATENT DOCUMENTS

| | | |
|---|---|---|
| EP | 0399227 | 11/1990 |
| EP | 0753737 | 1/1997 |

(Continued)

OTHER PUBLICATIONS

First Office Action from counterpart Chinese patent application No. 201180059710.6, Issuing date Feb. 24, 2014. 12 pages.

(Continued)

*Primary Examiner* — Nathan Bowers
*Assistant Examiner* — Lydia Edwards
(74) *Attorney, Agent, or Firm* — Christopher R. Christenson; Kelly, Holt & Christenson, PLLC (57) ABSTRACT

A pH sensing bioreaction system is provided. The system includes a bioreaction container having a plastic wall and a pH sensor attached to the plastic wall. The pH sensor includes a sensor body having a flange that is sealingly attached to the plastic wall. The sensor body has a reference electrolyte therein and a first sensing element disposed in the reference electrolyte. The first sensing element is configured to contact both the reference electrolyte and a sample solution inside the bioreaction container. A second sensing element is positionable into an interior of the bioreaction container. The pH sensor has a plurality of configurations that include a booted configuration in which at least one sensing element is isolated from the interior of the bioreaction container, and a service configuration in which the at least one sensing element is fluidically coupled to the interior of the bioreaction container.

14 Claims, 12 Drawing Sheets

(56) References Cited

U.S. PATENT DOCUMENTS

| | | | |
|---|---|---|---|
| 2001/0028865 A1 | 10/2001 | Cummings et al. | 422/103 |
| 2002/0072084 A1 | 6/2002 | Meserol et al. | 435/26 |
| 2003/0168403 A1 | 9/2003 | Corcho-Sanchez et al. | 210/631 |
| 2004/0140211 A1 | 7/2004 | Broy et al. | 204/424 |
| 2006/0228804 A1 | 10/2006 | Xu et al. | 436/84 |
| 2008/0032389 A1* | 2/2008 | Selker et al. | 435/283.1 |
| 2009/0130704 A1 | 5/2009 | Gyure | |

FOREIGN PATENT DOCUMENTS

| | | |
|---|---|---|
| EP | 2065701 | 6/2009 |
| EP | 2065701 A2 * | 6/2009 |
| GB | 2364125 | 1/2001 |
| JP | 2008039523 | 2/2008 |
| WO | WO 92/01218 | 1/1992 |
| WO | WO 2009/017765 | 2/2009 |

OTHER PUBLICATIONS

International Search Report and the Written Opinion from the related International patent application No. PCT/US2011/065032 dated Apr. 26, 2012.

International Search Report and the Written Opinion from the corresponding International patent application No. PCT/US2011/065033 dated Mar. 19, 2012.

Pharmaceutical Industry Solutions: Reliable Liquid Analysis. Brochure by Rosemount Analytical. Emerson Process Management, 2005.

S. Schmitmeier et al. "Development and Characterization of a Small-Scale Bioreactor Based on a Bioartificial Hepatic Culture Model for Predictive Pharmacological In Vitro Screenings", Biotechnology and Bioengineering, vol. 95, No. 6. Dec. 20, 2006.

Application Data Sheet. Tighter pH Control in Biopharmaceutical Applications. Jan. 2008 by Rosemount Analytical. Emerson Process Management.

Theory and Practice of pH Measurement. PN 44/6033/rev. D. Dec. 2010 by Rosemount Analytical. Emerson Process Management.

Related U.S. Appl. No. 13/325,260, filed 2012.

Office Action from Canadian patent application No. 2,818,943, dated Jul. 30, 2014. 2 pages.

Second Office Action from Counterpart Chinese Patent Application No. 201180059710.06 dated Aug. 22, 2014. 12 pages with English Translation.

* cited by examiner

PH SENSOR INTEGRATION TO SINGLE USE BIOREACTOR/MIXER

CROSS-REFERENCE TO RELATED APPLICATION

The present application is based on and claims the benefit of U.S. Provisional Patent Application Ser. No. 61/424,246, filed Dec. 17, 2010, the content of which is hereby incorporated by reference in its entirety.

BACKGROUND

The determination of pH is one of the most common process chemical measurements today. pH is a measure of a relative amount of hydrogen and hydroxide ions in an aqueous solution. In fermentation and cell culture, one of the most critical process challenges is to maintain the optimal pH level. Fermentation processes utilize a live organism, such as a yeast, bacteria, or fungus strain to produce an active ingredient. Fermentation processes normally have a relatively short duration (2-7 days). Cell culture is a process in which a mammalian cell is grown to produce an active ingredient. The cell culture process typically takes somewhat longer (2-8 weeks).

One significant challenge for pH measurement in the fermentation and cell culture fields is the cleaning processes involved with the fermenter or bioreactor. Specifically, the fermenter or bioreactor must be sterilized prior to the beginning of either process to ensure against cross batch contamination or any unwanted growths. In addition, pH sensors typically undergo a two point calibration using buffer solutions. The residual buffer chemicals must be removed prior to the beginning of a fermentation or culture batch. Such cleaning can include steaming the fermenter or bioreactor as well as the pH sensor. Exposure to high temperatures, steam and rapid thermal shock can significantly affect the sensor's life.

SUMMARY

A pH sensing bioreaction system is provided. The system includes a bioreaction container having a plastic wall and a pH sensor attached to the plastic wall. The pH sensor includes a sensor body having a flange that is sealingly attached to the plastic wall. The sensor body has a reference electrolyte therein and a first sensing element disposed in the reference electrolyte. The first sensing element is configured to contact both the reference electrolyte and a sample solution inside the bioreaction container. A second sensing element is positionable into an interior of the bioreaction container. The pH sensor has a plurality of configurations that include a booted configuration in which at least one sensing element is isolated from the interior of the bioreaction container, and a service configuration in which the at least one sensing element is fluidically coupled to the interior of the bioreaction container.

DETAILED DESCRIPTION OF ILLUSTRATIVE EMBODIMENTS

It is believed that there exists an emerging need for a disposable pH sensor which is compatible with a plastic bag type, ready to use, disposable bioreactor. Many glass electrode-based pH sensors require that the active surface or membrane of the sensor be protected from physical and environmental damage. This function is typically served by the disposable "boot" or cup placed over the sensing end of the sensor.

Embodiments of the present invention generally include a pH sensor that is installed on the wall of a single use bioreactor/mixer with a mechanical design that allows the booting solution stored around the pH sensing and reference element during sterilization (gamma irradiation), storage, and shipping of the single use bioreactor/mixer. The mechanical design also allows the storage chamber that retains the booting solution to be opened to expose the sensing and reference element prior to the operation.

Figure 1:
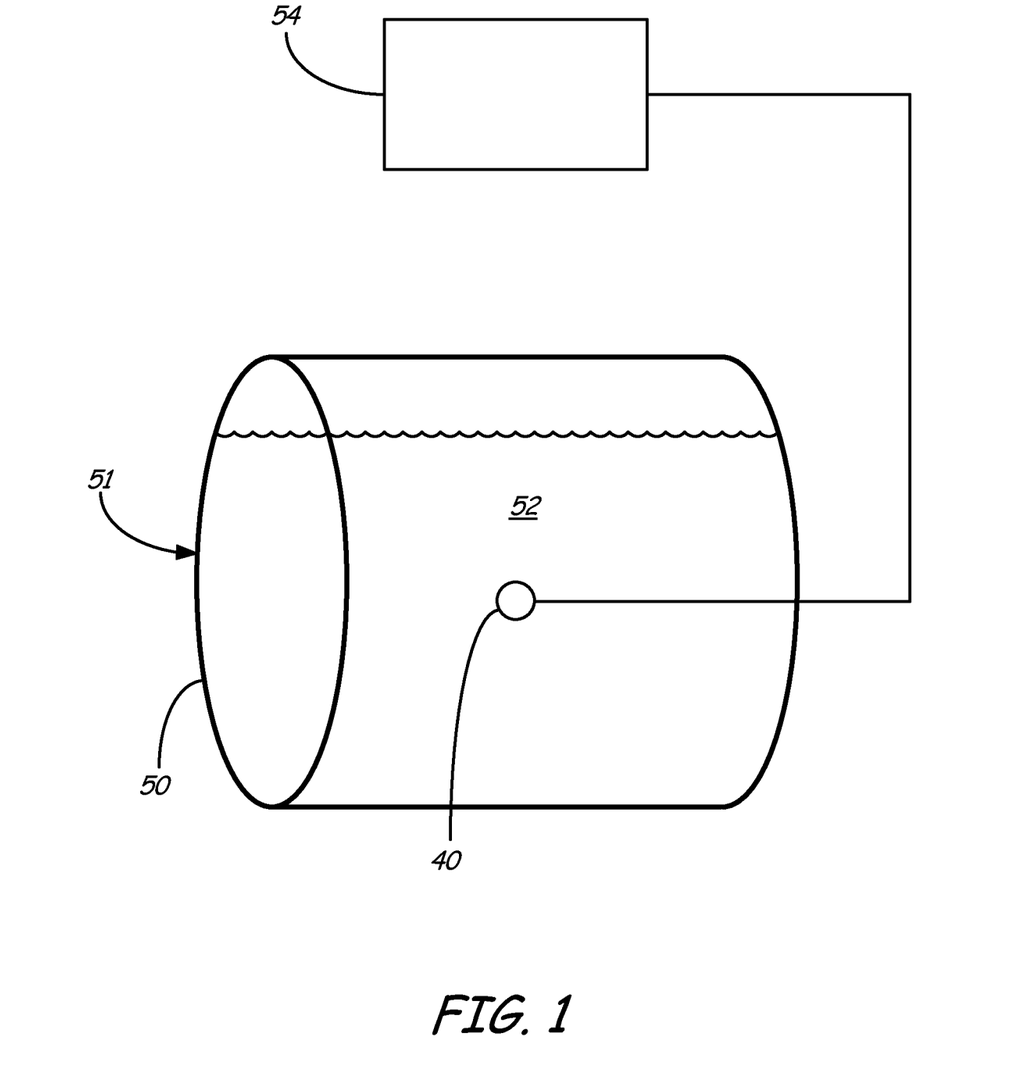
FIG. 1 is a diagrammatic view of a pH sensing bioreactor system with which embodiments of the present invention are particularly useful.

FIG. 1 is a diagrammatic view of a pH sensing bioreactor system with which embodiments of the present invention are particularly useful. pH sensor 40 is electrically coupled to pH analyzer 54 which may be any suitable pH analyzer or other electrical instrument. pH sensor 40 is physically attached to the wall 50 of single-use bioreactor/fermenter 51. A sample 52 is disposed within single use bioreactor 50 and is monitored, or otherwise measured, by pH sensor 40.

Embodiments of the present invention generally include a number of configurations in which a pH sensor can be used effectively with a single-use bioreactor.

Figure 2:
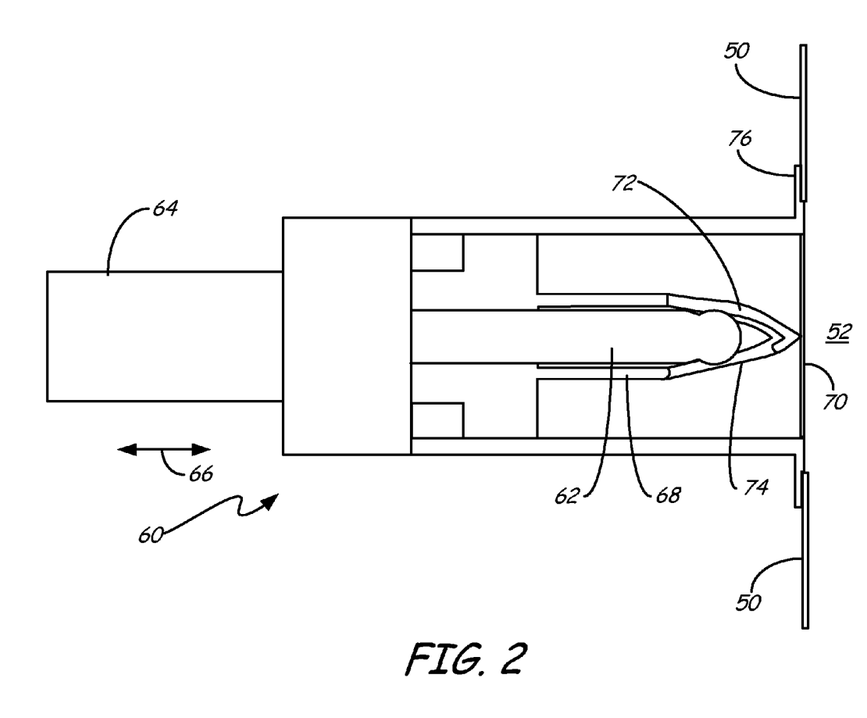
FIG. 2 is a diagrammatic cross sectional view of a pH sensor in accordance with an embodiment of the present invention in a booted position.
Figure 3:
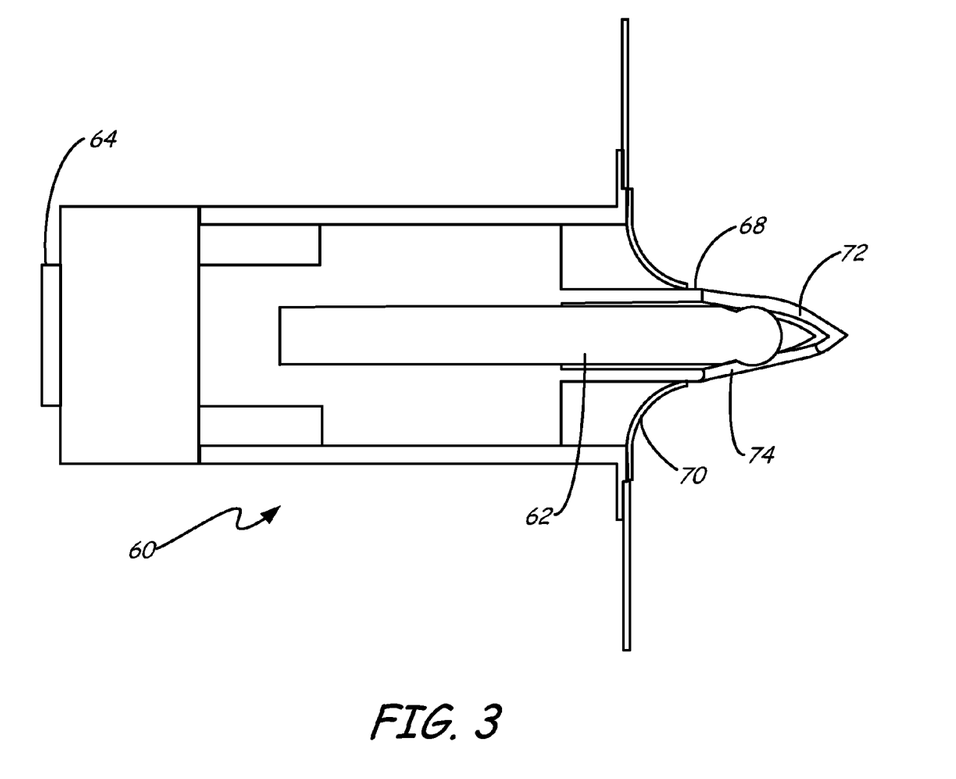
FIG. 3 is a diagrammatic cross sectional view of a pH sensor in accordance with an embodiment of the present invention in a service position.

FIG. 2 is a diagrammatic cross sectional view of a pH sensor 60 in accordance with an embodiment of the present invention. pH sensor 60 is illustrated in a "booted" position in that a sensing element, such as electrode 62, is separated from and not in contact with sample 52. As used herein, a sensing element is any electrode or portion of an electrode that may be exposed to a sample fluid and provide and electrical response thereto. Accordingly, a sensing element is intended to include glass bulb electrodes and reference junctions. pH sensor 60 includes plunger 64 that is coupled to electrode 62 such that axial movement of plunger 64 in the directions indicated at reference numeral 66 will generate corresponding movement of electrode 62. Electrode 62 is disposed within access spear 68. Access spear 68 is designated as such because it is physically shaped like a spear such that suitable actuation of plunger 64 will cause access spear 68 to pierce through rubber membrane 70. When access spear 68 is pierced through rubber membrane 70, ports 72, 74 allow sample 52 to come into contact with electrode 62. When access spear 68 pierces rubber membrane 70, pH sensor 60 is said to be in a service position. Such configuration is illustrated in FIG. 3.

pH sensor 60 includes flange 76 that is fused, adhered, or otherwise bonded to wall 50 of the bioreactor 51. In the embodiment illustrated in FIG. 2, flange 76 is bonded to the outside surface of wall 50. However, embodiments of the present invention also include flange 76 being bonded to an inside surface of wall 50. Flange 76 can be thermally welded, or otherwise permanently attached, to sidewall 50 of bioreactor 51 in any suitable manner.

Figure 4:
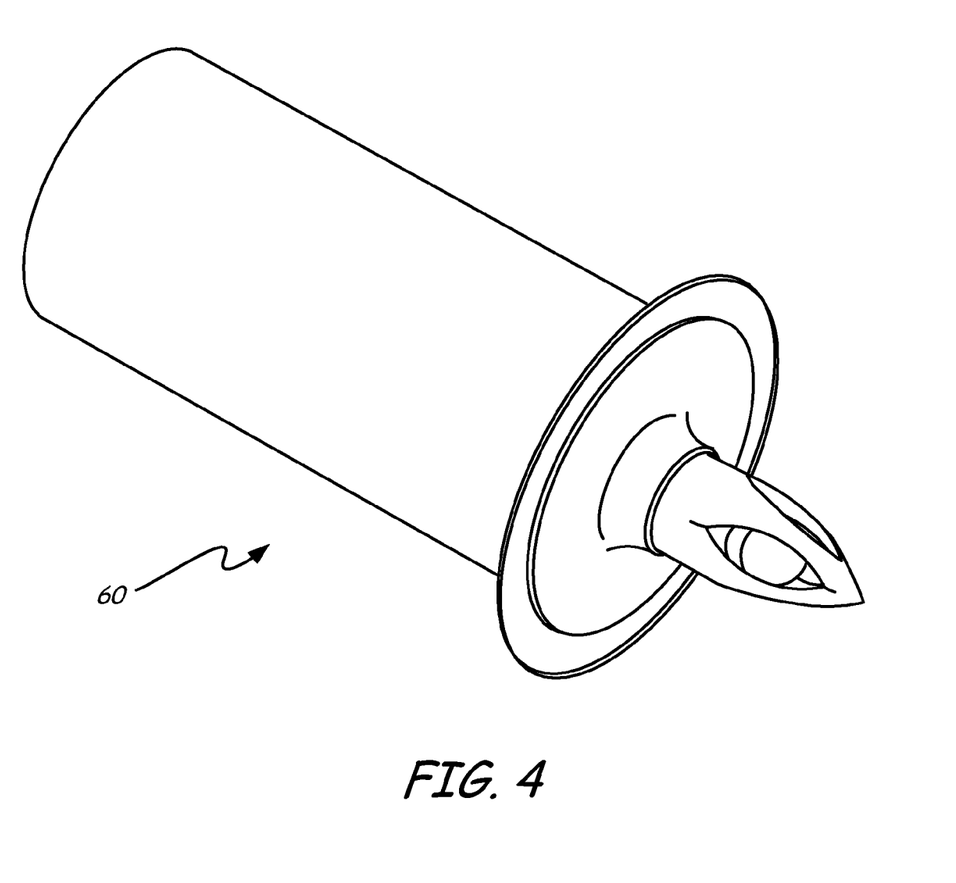
FIG. 4 is a diagrammatic perspective view of pH sensor in accordance with embodiment of the present invention shown in the service position.

FIG. 4 is a diagrammatic perspective view of pH sensor 60 in accordance with one embodiment of the present invention shown in the service position.

Figure 5:
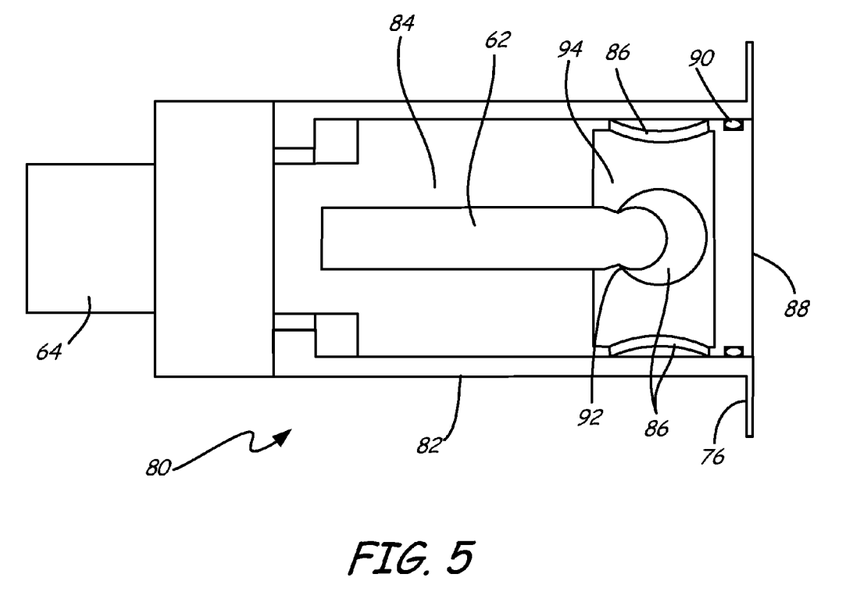
FIG. 5 is a diagrammatic cross sectional view of a pH sensor in accordance with another embodiment of the present invention.

FIG. 5 is a diagrammatic cross sectional view of a pH sensor 80 in accordance with another embodiment of the present invention. pH sensor 80 bears some similarities to pH sensor 60, and like components are number similarly. pH 80 includes a sensor body 82 through which plunger 64 may axially translate electrode 62. Plunger 64 is coupled to spool 84 to which electrode 62 is affixed. Spool 84 includes a plurality of apertures 86 and end cap 88. End cap 88 is fluidically sealed against an internal sidewall of body 82 by o-ring seal 90. As shown in FIG. 5, in the booted position, a sensing element, such as distal sensing portion 92, of electrode 62 is disposed within a chamber bound by surface 94 of spool 84, cap 88, and portions of housing 82. The chamber within which distal sensing portion 92 of electrode 62 resides can be filled with a booting solution, if necessary. When the pH sensor is ready to be used, plunger 64 is advanced thereby pressing end cap 88 beyond flange 76.

Figure 6:
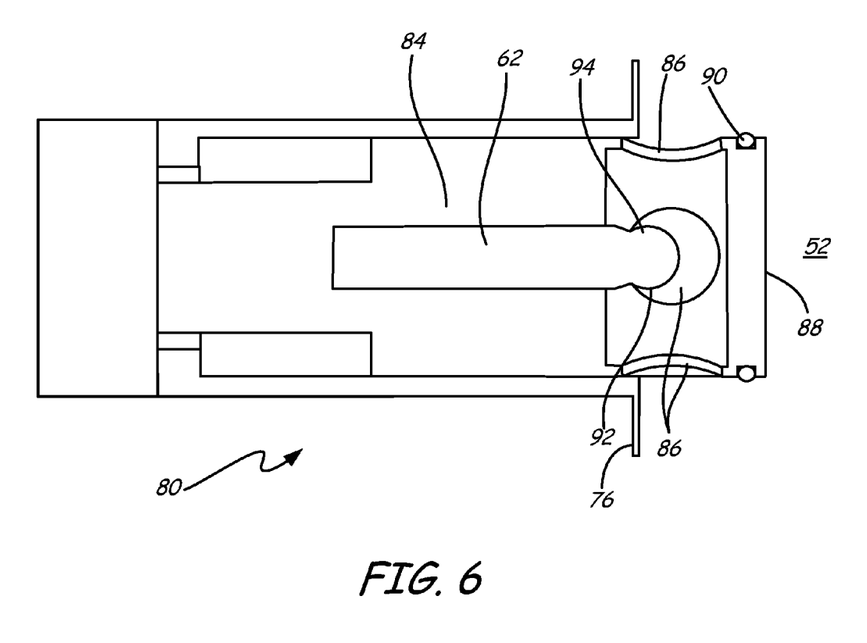
FIG. 6 is a diagrammatic view of a pH sensor arranged in an in-service position in accordance with an embodiment of the present invention.

FIG. 6 is a diagrammatic view of pH sensor 80 arranged in an in-service position. In this position, plunger 64 has been advanced to drive end cap 88 beyond flange 76. As illustrated in FIG. 6, apertures 86 now allow fluidic communication between distal sensing portion 92 and sample 52 in the bioreactor.

Figure 7:
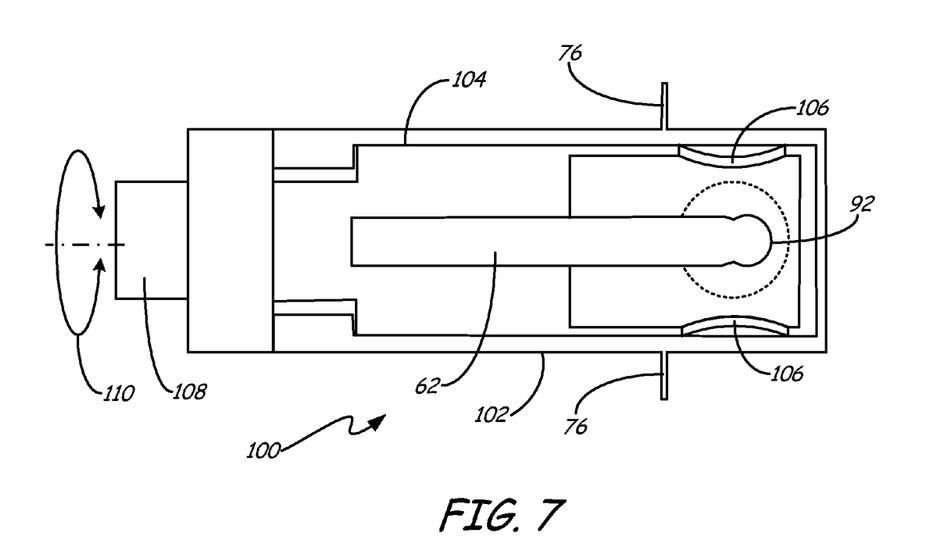
FIG. 7 is a diagrammatic cross sectional view of a pH sensor in accordance with another embodiment of the present invention in a booted position.
Figure 8:
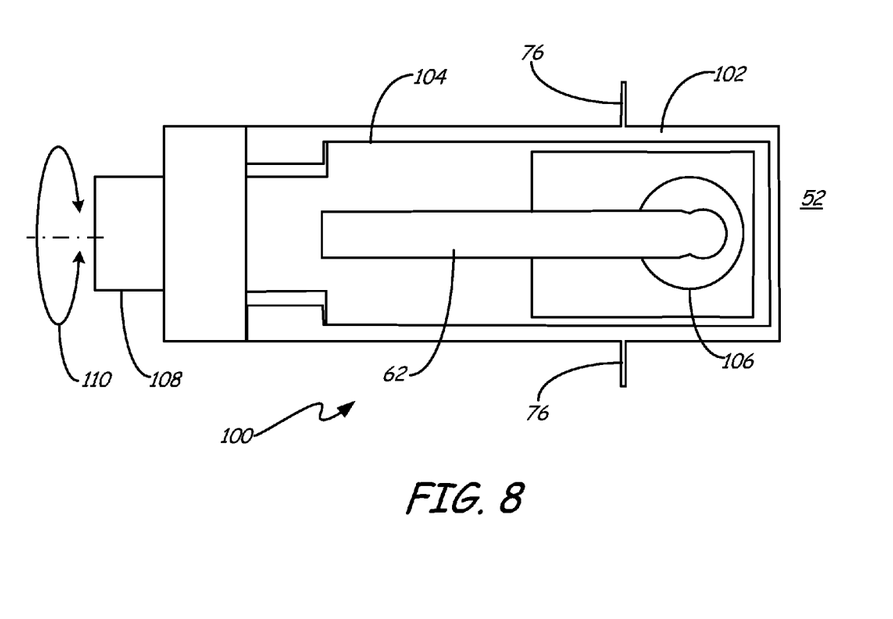
FIG. 8 is a diagrammatic cross sectional view of a pH sensor in accordance with another embodiment of the present invention in a service position.

FIG. 7 is a diagrammatic cross sectional view of a pH sensor in accordance with another embodiment of the present invention. pH sensor 100 includes a sensor body 102 to which flange 76 is mounted. As with previous embodiments, flange 76 is generally permanently attached to a wall of a bioreactor via any suitable method, such as thermal welding. Plug 104 is rotatably disposed within sensor body 102 and maintains electrode 62 therein. Plug 104 generally defines a chamber near distal, sensing end 92 of electrode 62. Plug 104 includes one or more fluid access ports 106 which are generally blocked, or otherwise occluded, from communicating with a sample when the sensor is in the booted position, as shown in FIG. 7. In order to change from the booted position to the service position, knob 108 is rotated in the direction indicated by arrow 110, which rotation in turn, rotates plug 104. Upon suitable rotation, sensor 100 enters the service position, as shown in FIG. 8. In this position, one or more of access apertures 106 at least partially aligns with an access port in sensor body 102 thereby allowing fluidic communication between sensing end 92 and sample 52.

Figure 9:
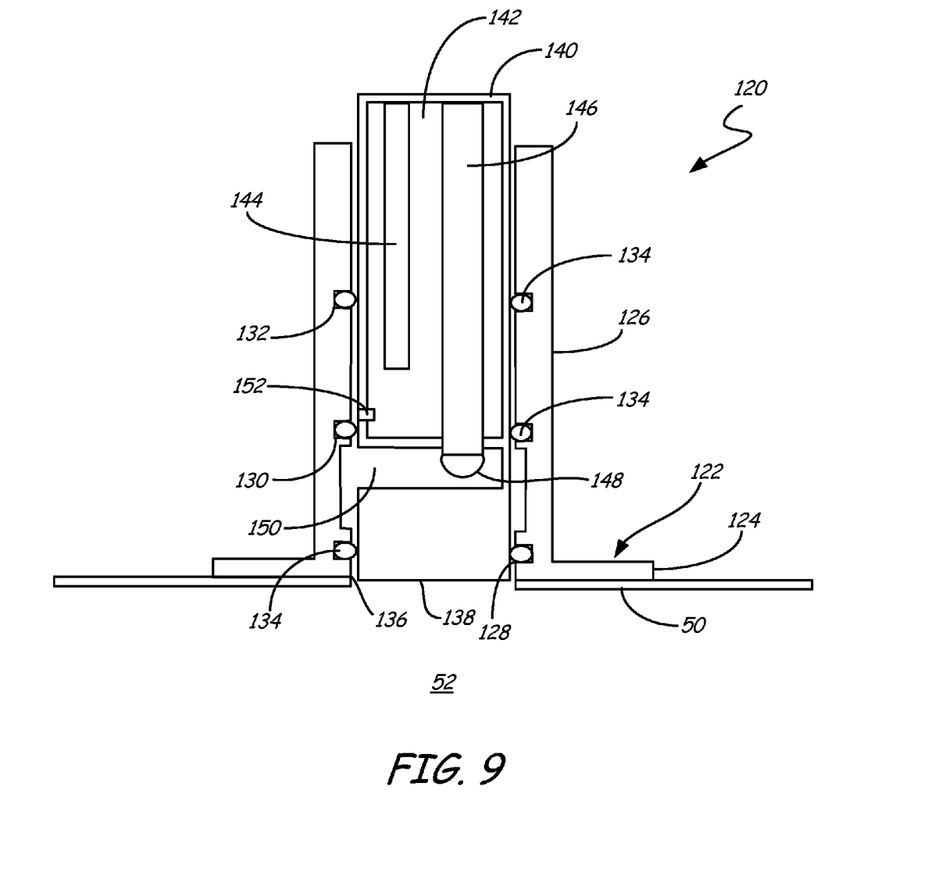
FIG. 9 is diagrammatic view of a pH sensor integrated with a single-use bioreactor/mixer in accordance with an embodiment of the present invention in a booted position.

FIG. 9 is diagrammatic view of a pH sensor 120 integrated with a single-use bioreactor/mixer in accordance with an embodiment of the present invention. Sensor 120 includes flange/support 122 that includes flange 124 coupled to wall 50 of a single-use bioreactor/mixer. Flange 124 is also coupled to support sleeve 126 that illustratively includes three o-ring groves 128, 130, and 132 on an internal surface thereof. An o-ring 134 is disposed within each of groves 128, 130, 132.

Flange 124 is preferably thermally welded, or permanently attached via some other suitable method, to wall 50 of the single-use bioreactor. Additionally, wall 50 includes an aperture 136 that has an inside diameter that is larger than the outside diameter of endcap 138. pH sensor 120 also includes sensor body 140 which contains a suitable reference electrolyte 142 and reference electrode 144. Additionally, sensing element (glass electrode) 146 is disposed, at least partially, within sensor body 140 and extends such that distal sensing portion 148 is disposed within storage chamber 150 when the sensor is in the booted position as illustrated in FIG. 9. Additionally, a sensing element, such as reference junction 152 is physically isolated from storage chamber 150.

The sensor design provides a number of positions that are useful in combination with a single-use bioreactor. In a first position (shown in FIG. 9) the sensor is in a booted position where the sensing portion 148 is protected from damage and may also be stored in a booting solution that is provided within storage chamber 150. In a second position, (described in further detail with respect to FIG. 10) the reference junction is placed in the booting solution for sensor calibration purposes. In a third position (described with respect to FIG. 11), the storage chamber 150 is opened into sample 52, to expose sensing element 148, and reference junction 152 to sample 52.

Figure 10:
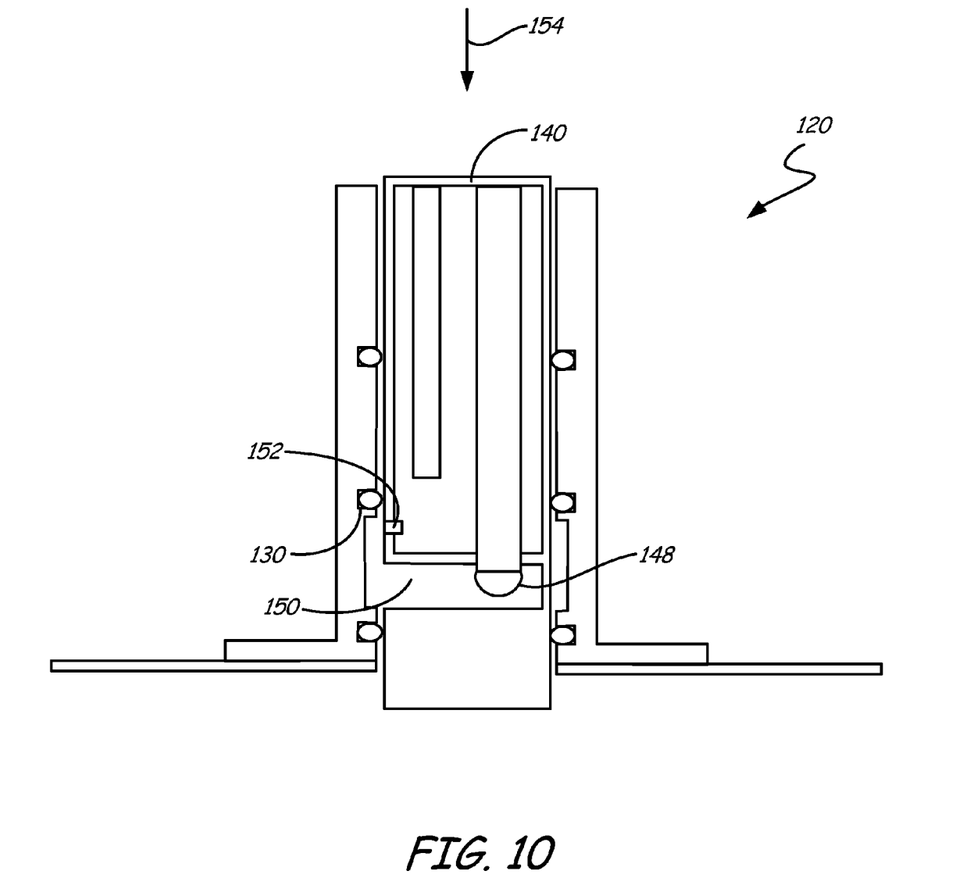
FIG. 10 is diagrammatic view of a pH sensor integrated with a single-use bioreactor/mixer in accordance with an embodiment of the present invention in a calibration position.

FIG. 10 is diagrammatic view of pH sensor 120 arranged in the second (calibration) position. In the configuration shown in FIG. 10, sensor body 140 has been displaced in the direction of arrow 154 to such an extent that reference junction 152 has passed beyond o-ring grove 130. As such, reference junction 152 is in fluidic communication with sensing portion 148 of sensing electrode 146. Additionally, storage chamber 150 is still fluidically isolated from sample 52 by virtue of the o-ring disposed within o-ring grove 134. Given that the booting solution within storage chamber 150 can be provided having a precisely known pH, sensor 120 can be calibrated to ensure that its output corresponds with the known pH of the booting solution.

Figure 11:
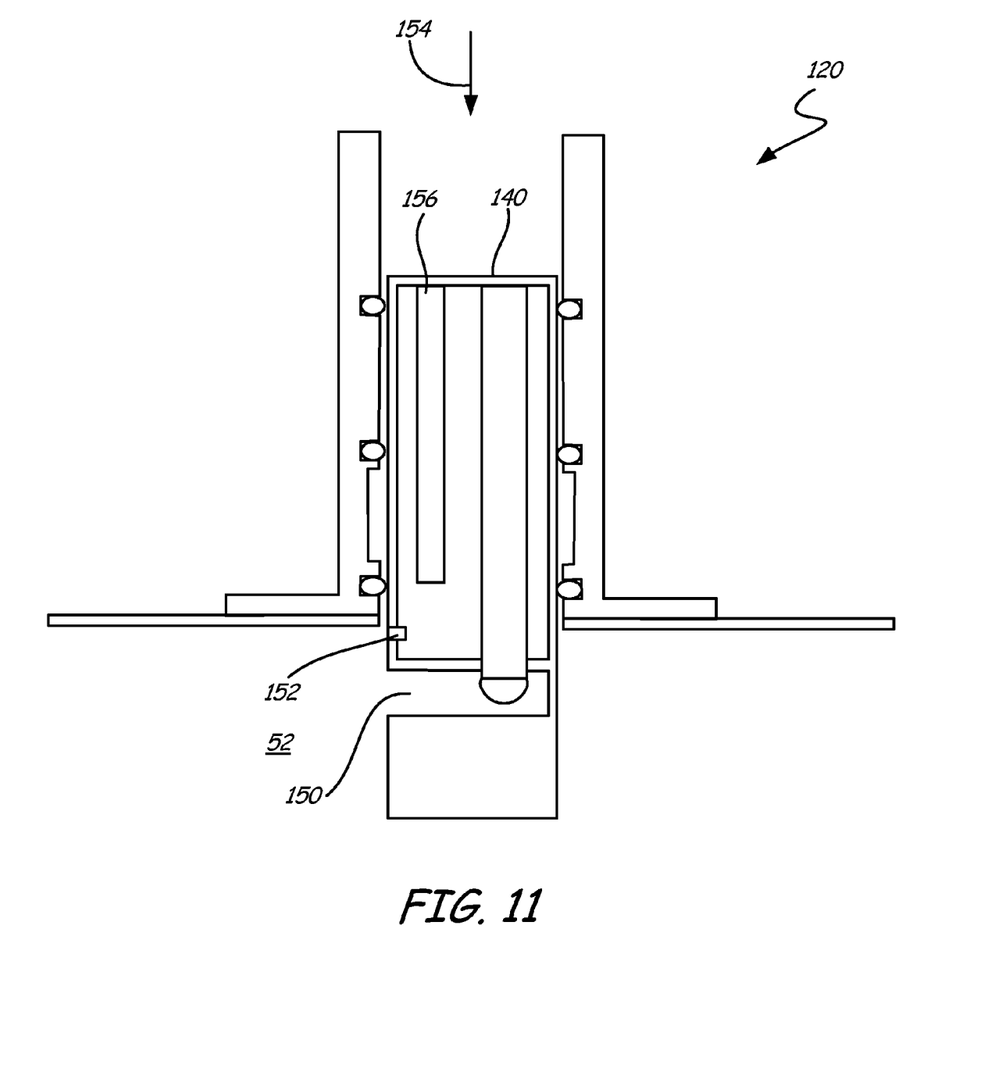
FIG. 11 is diagrammatic view of a pH sensor integrated with a single-use bioreactor/mixer in accordance with an embodiment of the present invention in a service position.

FIG. 11 is a diagrammatic view of pH sensor 120 in the service position. Sensor body 140 has moved axially in the direction of arrow 154 to such an extent that storage chamber 150 is now opened to sample 52. Moreover, reference junction 152 is also disposed within sample 52. In this configuration, sensing electrode 146 will provide an indication, in combination with reference electrode 156 that is indicative of the pH of sample 52.

Figures 12, 13, 14A:
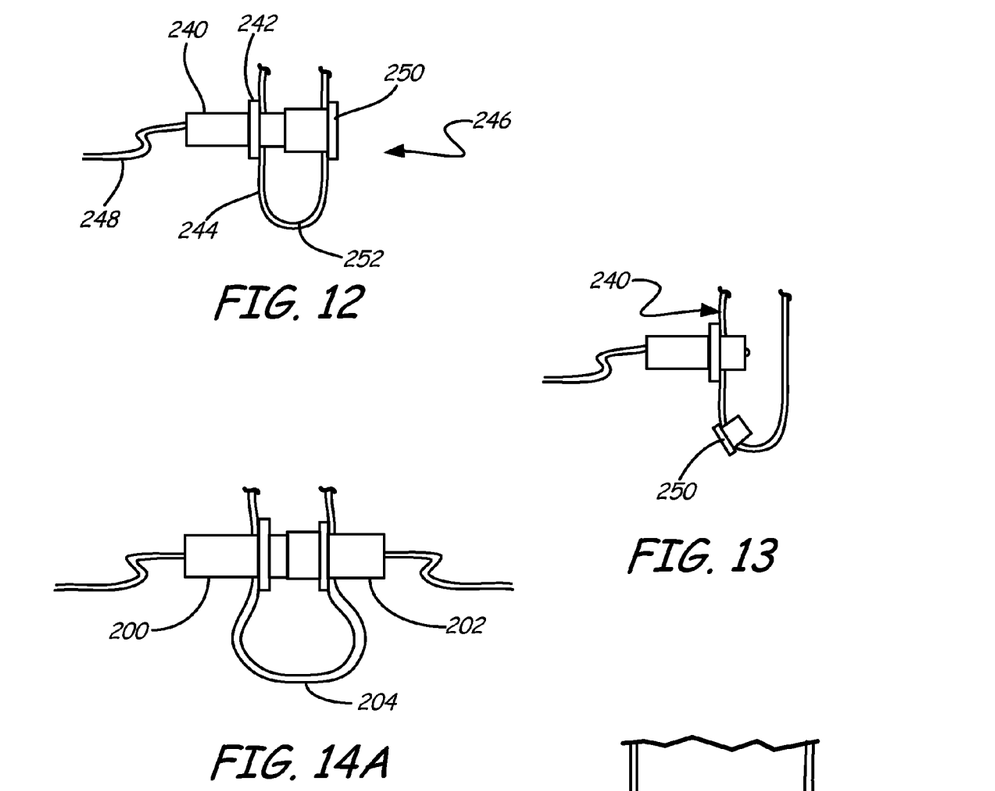
FIG. 12 is a diagrammatic view of a pH sensor and boot integrated into a wall of a sing-use bioreactor in accordance with an embodiment of the present invention in a booted configuration.
FIG. 13 is a diagrammatic view of a pH sensor and boot integrated into a wall of a sing-use bioreactor in accordance with an embodiment of the present invention in a service configuration.
FIGS. 14A and 14B are diagrammatic views of a pH sensor coupled to another process analytic sensor where each sensor includes a flange that is welded, or otherwise bonded or fixed to a wall of a single-use bioreactor/mixer in accordance with an embodiment of the present invention.

FIG. 12 is a diagrammatic view of a pH sensor and boot integrated into a wall of a sing-use bioreactor in accordance with an embodiment of the present invention. pH sensor 240 includes flange 242 that is coupled to, preferably via thermal welding, sidewall 244 of single-use bioreactor 246. Sensor 240 includes cabling 248 that is coupled to a suitable analyzer, such as analyzer 54. Sidewall 244 is also coupled (preferably via thermal welding) to sensor boot 250. Sidewall 244 includes a fold 252 that allows boot 250 to engage and protect the sensing end of sensor 240. As illustrated in FIG. 13, a user can simply grasp boot 250 through the flexible sidewall 144 of bioreactor 246 and remove boot 250 from sensor 240. Such removal thereby exposes the pH membrane and reference junction of pH sensor 240 to the interior of the single-use bioreactor/mixer 246.

Figure 14B:
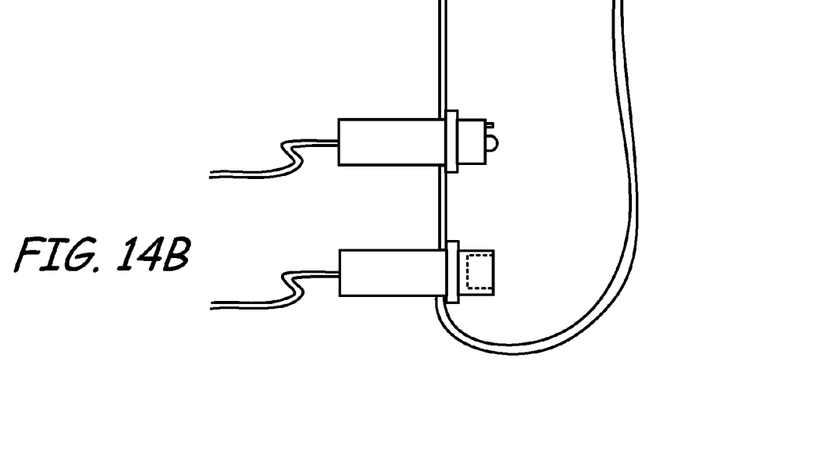

The cap or boot can actually be integrated with a second process analytic sensor, such as a dissolved oxygen sensor. In this manner, when pH sensor and dissolved oxygen sensor are decoupled for one another, both sensors are thereby prepared for use. FIG. 14A is a diagrammatic view of a pH sensor 200 coupled to a dissolved oxygen sensor 202 where each sensor includes a flange that is welded, or otherwise bonded to bag film 204 to form a fluid-tight seal. Bag film 204 is folded such that pH sensor 200 can be coupled to a portion of dissolved oxygen sensor 202, which can also act as a boot to pH sensor 200. When operation of the sensors is required, the two sensors can simply be grasped and pulled apart from one another to yield the configuration shown in FIG. 14B.

Although the present invention has been described with reference to preferred embodiments, workers skilled in the art will recognize that changes may be made in form and detail without departing from the spirit and scope of the invention.

What is claimed is:

1. A pH sensing bioreaction system comprising:
a bioreaction container having a plastic wall;
a pH sensor including:
a sensor body mounted substantially external to the bioreaction container and having a flange sealingly attached to the plastic wall;
a first sensing element being configured to contact a sample solution inside the bioreaction container when the pH sensor is in a service configuration;
a second sensing element being positionable into an interior of the bioreaction container; and
wherein the pH sensor has a plunger axially movable within the sensor body, the plunger having a first axial position in which at least one sensing element is isolated from the interior of the bioreaction container, and a second axial position in which the first and second sensing elements are fluidically coupled to the interior of the bioreaction container.

2. The system of claim 1, wherein the pH sensor is adapted to change configurations without requiring user access to the interior of the bioreaction container.

3. The system of claim 1, wherein the plunger seals to the sensor body in all axial positions.

4. The system of claim 1, wherein the flange is thermally welded to the plastic wall of the bioreaction container.

5. The system of claim 1, wherein the at least one sensing element includes a glass bulb electrode.

6. The system of claim 5, wherein the at least one sensing element further includes a reference junction.

7. The system of claim 1, wherein the at least one sensing element includes a reference junction.

8. The system of claim 1, and further comprising an o-ring sealing an external surface of a distal portion of the plunger to an internal distal portion of the sensor body when the plunger is in the first axial position.

9. A pH sensing bioreaction system comprising:
a bioreaction container having a plastic wall;
a pH sensor including:
a sensor body mounted substantially external to the bioreaction container and having a flange sealingly attached to the plastic wall, the sensor body being coupled to a membrane that seals an interior of the sensor body from the bioreaction container;
a first sensing element being configured to contact a sample solution inside the bioreaction container when the pH sensor is in a service configuration;
a second sensing element being positionable into an interior of the bioreaction container; and
wherein the pH sensor has an access spear that is configured to pierce the membrane and allow contact between the first and second sensing elements and the interior of the bioreaction container.

10. A pH sensing bioreaction system comprising:
a bioreaction container having a plastic wall;
a pH sensor including:
a sensor body mounted substantially external to the bioreaction container and having a flange sealingly attached to the plastic wall;
a first sensing element configured to contact a sample solution inside the bioreaction container when the pH sensor is in a service configuration;
a second sensing element being positionable into an interior of the bioreaction container; and
wherein the pH sensor has plug that is rotatable within the sensor body, the plug having a first rotational orientation in which at least one sensing element is isolated from the interior of the bioreaction container, and a second rotational orientation in which the first and second sensing elements are fluidically coupled to the interior of the bioreaction container.

11. A pH sensing bioreaction system comprising:
a bioreaction container having a plastic wall;
a pH sensor including:
a flange sealingly attached to the plastic wall;
a sensor body slidably disposed within the flange external to the bioreaction container, the sensor body having at least one seal interposed between the sensor body and the flange;
a first sensing element being configured to contact both a sample solution inside the bioreaction container when the pH sensor is in a service configuration;
a second sensing element being positionable into an interior of the bioreaction container; and
wherein the pH sensor has sensor body has a plurality of axial positions, a first axial position in which the first and second sensing elements are isolated from the interior of the bioreaction container, and a second axial position in which the first and second sensing elements are fluidically coupled to the interior of the bioreaction container.

12. The system of claim 11, wherein the sensor body has a third axial position in which the first and second sensing elements are isolated from the interior of the bioreaction container but disposed in contact with a fluid of known pH.

13. The system of claim 12, wherein the pH sensor is transitioned from the first axial position to the third axial position by axially translating the sensor body with respect to the flange.

14. The system of claim 13, wherein the pH sensor is transitioned from the third axial position to the second axial position by axially translating the sensor body with respect to the flange.

* * * * *

UNITED STATES PATENT AND TRADEMARK OFFICE
CERTIFICATE OF CORRECTION

PATENT NO. : 8,900,855 B2
APPLICATION NO. : 13/325254
DATED : December 2, 2014
INVENTOR(S) : Chang-Dong Feng et al.

Page 1 of 1

It is certified that error appears in the above-identified patent and that said Letters Patent is hereby corrected as shown below:

In the Claims

Column 6

Claim 10:
Line 29:
insert --a-- between "has" and "plug"

Claim 11:
Line 48:
after "wherein the pH sensor" remove "has sensor"

Signed and Sealed this
Twenty-eighth Day of June, 2016

Michelle K. Lee
*Director of the United States Patent and Trademark Office*